United States Patent
Wu

(10) Patent No.: US 7,547,518 B2
(45) Date of Patent: *Jun. 16, 2009

(54) METHOD OF SCREENING ENDOTHELIAL CELLS FOR ANGIOGENIC CAPABILITY

(75) Inventor: Min Wu, Carlisle, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 237 days.

This patent is subject to a terminal disclaimer.

(21) Appl. No.: 10/913,209

(22) Filed: Aug. 6, 2004

(65) Prior Publication Data

US 2005/0064523 A1 Mar. 24, 2005

Related U.S. Application Data

(60) Provisional application No. 60/496,308, filed on Aug. 19, 2003.

(51) Int. Cl.
*G01N 33/53* (2006.01)
*G01N 33/533* (2006.01)
*G01N 33/577* (2006.01)
*C12P 21/08* (2006.01)
*C07K 16/28* (2006.01)

(52) U.S. Cl. .................. 435/7.1; 435/7.21; 435/7.92; 435/7.5; 530/387.1; 530/388.22; 530/389.1; 530/391.3

(58) Field of Classification Search .................. None
See application file for complete search history.

(56) References Cited

U.S. PATENT DOCUMENTS 6,524,583 B1 2/2003 Thorpe et al.

OTHER PUBLICATIONS

Asahara et al, Science 275: 964-967, Feb. 1997.*
Perichev et al, Blood 95(3): 952-958, Feb. 2000.*
Richard et al, Experimental Cell Research 240: 1-6, 1998.*
Harlow et al, in Antibodies a Laboratory Manual, 1988, Cold Spring harbor laboratory publication, Cold Spring Harbor, NY, pp. 321-323 and 409-410.*
Khan et al, Clinical Cytometry 64B: 1-8, 2005.*
Yang et al, Arterioscler Thromb Vasc Biol 21: 1934-1940, 2001.*
Peichev et al, Blood 95(3): 952-958, Feb. 2000.*
Favier, et al., Angiogenesis and Vascular Architecture in Pheochromocytomas, American Journal of Pathology, Oct. 2002, pp. 1235-1246, vol. 161, No. 4.
Favre, Expression of genes involved in vascular development and angiogenesis in endothelial cells of adult lung, AJP-Heart and Circulatory Physiology, Nov. 2003, pp. 1917-1938, vol. 285.
Sato, Correlations of the Expression of Fibroblast Growth Factor-2, Vascular Endothelial Growth Factor, and their Receptors with Angiogenesis in Synovial Tissues from Patients with Internal Derangement . . . , J Dent Res, 2003, pp. 272-277, vol. 82(4).
Takeshita, Intramuscular Administration of Vascular Endothelial Growth Factor Induces Does-Dependent Collateral Artery Augmentation in a Rabbit Model of Chronic Limb Ischemia, Circulation, 1994, pp. II-228, vol. 90, No. 5//PT2.
Folkman, Tumor Angiogenesis: Therapeutic Implications, New England Journal of Medicine, Nov. 18, 1971, pp. 1182-1186, vol. 285, No. 21.

* cited by examiner

*Primary Examiner*—Phuong Huynh
(74) *Attorney, Agent, or Firm*—Hoffmann & Baron, LLP

(57) ABSTRACT

Provided is a method of screening a primary endothelial cell population for angiogenesis capability comprising: (a) measuring the percentage of cells that are positive for VEGF R2 and CD34, the level of VEGF R2, or measuring the VEGF R2 to VEGF R1 ratio in the population; and (b) selecting those populations where the measured percentage or the measured ratio is over a threshold value.

9 Claims, No Drawings

METHOD OF SCREENING ENDOTHELIAL CELLS FOR ANGIOGENIC CAPABILITY

This application claims priority of U.S. Provisional Patent Application No. 60/496,308, filed Aug. 19, 2003, which is hereby incorporated by reference.

BACKGROUND OF THE INVENTION

1. Field of the Invention

The present invention is generally directed to methods of identifying highly angiogenic endothelial cells. In particular, the present invention is directed to a method of screening endothelial cells for angiogenic capability comprising quantifying the endothelial cells that are VEGF R2 positive and CD34 positive, the VEGRF 2 amount, or determining the VEGF R2 to VEGF R1 ratio or number of VEGF-R2 positive cells to number of VEGF-R1 positive cells.

2. Background of the Invention

Endothelial cells that form the lining of blood vessels are well known for their capacity to adjust their numbers and arrangement to suite local requirements. All tissues depend on a blood supply and the blood supply depends on endothelial cells. Blood vessels create an adaptable life support system in every region of the body. If not for endothelial cells extending and maintaining this network of blood vessels, tissue growth and repair would not be possible.

The largest blood vessels are arteries and veins, which have a thick tough outer wall of connective tissue and smooth muscle. The wall is lined by a thin single layer of endothelial cells, separated from the surrounding outer layers by a basal lamina. While the amounts of connective-tissue and smooth muscle in the vessel wall may vary according to the vessel's diameter and function, the endothelial lining is always present. In the smaller capillaries and sinusoids, the walls consist solely of endothelial cells and basal lamina. Thus, endothelial cells line the entire vascular system. Studies have shown that arteries and veins develop from small vessels constructed solely of endothelial cells and a basal lamina, connective tissue and smooth muscle being added later where required upon signals from the endothelial cells.

Throughout the vascular system endothelial cells retain a capacity for cell division and movement. The is important in repair and maintenance of the vascular system. For example, if a part of the wall of a blood vessel is damaged and loses endothelial cells, neighboring endothelial cells will proliferate and migrate in to cover the exposed surface. Newly formed endothelial cells have also been know to cover the inner surface of plastic tubing used by surgeons to replace damaged blood vessels.

Endothelial cells not only repair damaged blood vessels, they also create new blood vessels. They do this in embryonic tissues to support growth, in normal adult tissue for repair and maintenance, and in damaged tissue to support repair. This process is called angiogenesis.

Angiogenesis is the fundamental process by which new blood vessels are formed. This process is essential in numerous normal physiological phenomena such as embryonic development, tissue growth, tissue remodeling, and wound healing. Angiogenesis is also important in certain pathological events. In addition to a role in solid tumor growth and metastasis, other notable conditions with an angiogenic component are arthritis, psoriasis and diabetic retinopathy. In other pathologies such as the cardiovascular diseases, the diseases of the peripheral arteries as well as the vascular and cerebral lesions, angiogenesis can present an important therapeutic base. The promotion of angiogenesis in the damaged locations can lead to formation of sanguineous neovessels that are lateral and alternative to the damaged vessels, thereby providing blood and, thus, oxygen and other nutritive and biological factors necessary for the survival of the tissues involved.

During the process of angiogenesis, endothelial cells, which exist in a quiescent state as part of an existing blood vessel, grow and enter a migratory, proliferative state. This migratory, proliferative state is eventually resolved when the cells differentiate into capillary tubes and return to the quiescent state as part of a functional new blood vessel. The process of angiogenesis is orchestrated by a complex network of multiple macromolecular interactions. Some essential angiogenic factors include fibroblast growth factor-basic (bFGF), vascular endothelial growth factor (VEGF), the angiopoietins, cytokines, extracellular matrix proteins, and matrix metalloproteases. These factors are produced locally by stromal cells (e.g., smooth muscle cells, pericytes, fibroblasts) and by activated leukocytes that are recruited to the area. A feature of endothelial cells is their capacity to undergo tubulogenesis, an aspect of angiogenesis, under appropriate conditions.

Angiogenesis is regulated in both normal and malignant tissues by the balance of angiogenic stimuli and angiogenic inhibitors that are produced in the target tissue and at distant sites. Vascular endothelial growth factor-A (VEGF, also known as vascular permeability factor, VPF) is a primary stimulant of angiogenesis. VEGF is a multifunctional cytokine that is induced by hypoxia and oncogenic mutations and can be produced by a wide variety of tissues.

Angiogenesis is stimulated and harnessed by some neoplasms (e.g., tumors) to increase nutrient uptake. However, in contrast to normal angiogenesis, which leads to anastomoses (i.e., vessel connections) and capillary maturation, angiogenesis associated with neoplasia is a continuous process. Endothelial cells are activated by nearby neoplastic cells to secrete not only VEGF which stimulates angiogenesis, but also matrix metalloproteases (MMP) which degrade the surrounding extracellular matrix. The endothelial cells then invade the extracellular matrix where they proliferate, migrate, and organize to form new blood vessels, which support neoplasm growth and survival.

The newly vascularized neoplasm continues to grow, leading to further nutrient deprivation and chronic pro-angiogenic signaling. The vasculature of neoplasms is characterized by the presence of structural irregularities (lacunae) and a low rate of formation of inter-vessel connections. This partially dysfunctional vasculature fuels the permanent requirement for angiogenesis. Additionally, this incomplete vasculature is believed to promote the shedding of neoplastic cells into the systemic circulation. Hence, the angiogenic potential of a neoplasm correlates with metastatic potential. As a significant proportion of neoplasms are dependent on continued angiogenesis, inhibition of angiogenesis blocks neoplasm growth which often leads to complete necrosis of the neoplasm.

The interplay of growth factors (e.g., VEGF) and surface protein extracellular interactions drive the process of angiogenesis through a predictable sequence of events. Activation of endothelial cells by pro-angiogenic stimuli results in vasodilation, hyperpermeability, and local release of proteases which degrade the basement membrane and extracellular membrane (ECM). This allows the formation of a provisional fibrin matrix, which provides a primary scaffold for the assembly of early microvessels. Motogenic endothelial cells sprout into the matrix and migrate with controlled matrix degradation at the tip. Proliferation occurs proximal to migration with formation of a primitive tube. Extensive remodeling ensues until the new capillary matures and anastomoses (i.e., fuses and joins) with other sprouts.

VEGF is critical to the angiogenesis process. VEGF induces angiogenesis and endothelial cell proliferation and it plays an important role in regulating vasculogenesis. VEGF is a heparin-binding glycoprotein that is secreted as a homodimer of 45 kDa. Most types of cells, but usually not endothelial cells themselves, secrete VEGF. VEGF is known to increase vascular permeability and cause vasodilatation, partly through stimulation of nitric oxide synthase in endothelial cells. VEGF can also stimulate cell migration and inhibit apoptosis. There are three receptors in the VEGF receptor family (VEGF R1, VEGF R2 and VEGF R3). These receptors have the common properties of multiple immunoglobulin G (IgG)-like extracellular domains and tyrosine kinase activity. Endothelial cells also express additional VEGF receptors, Neuropilin-1 and Neuropilin-2. VEGF-A is the most commonly occurring VEGF. VEGF-B through VEGF-D are lesser occurring. VEGF-A binds to VEGF R1 and VEGF R2 and to Neuropilin-1 and Neuropilin-2. Placental Growth Factor (PlGF) and VEGF-B bind VEGF R1 and Neuropilin-1. VEGF-C and -D bind VEGF R3 and VEGF R2. VEGF R1 and VEGF R2 are upregulated on tumor and proliferating endothelium, partly by hypoxia and also in response to VEGF-A itself. VEGF R1 and VEGF R2 can interact with multiple downstream signaling pathways via proteins such as PLC, Ras, Sic, Nck, PKC and PI3-kinase. VEGF R1 is of higher affinity than VEGF R2 and mediates motility and vascular permeability. VEGF R2 is necessary for proliferation.

The therapeutic implications of angiogenic growth factors were first described by more than 30 years ago. (Folkman, N. Engl. J. Med., 85:1182-1186 (1971)). Recent work has established the feasibility of using recombinant angiogenic growth factors, such as vascular endothelial growth factor (VEGF-1) to expedite and/or augment collateral artery development in animal models of myocardial and hindlimb ischemia (Takeshita, et al., Circulation, 90:228-234 (1994) and Takeshita, et al., J Clin Invest, 93:662-70 (1-994)). However, alternative methods for promoting angiogenesis are desirable for a number of reasons. For example, it is believed that native endothelial cell number and/or viability decreases over time. Thus, in certain patient populations, e.g., the elderly, cells capable of responding to angiogenic proteins may be limited. These problems can be reduced by administering isolated endothelial cells to patients undergoing treatment for ischemic disease. However, prior to the present invention, such methods were prohibitively expensive as they required expensive isolation and maintenance of cells.

Angiogenesis or angiogenic capability refers to the capacity of an endothelial cell to generate new capillary blood vessels. Highly angiogenic endothelial cells have a wide spectrum of uses including, use in the prevention or treatment of trauma, graft rejection, cerebrovascular ischemia, renal ischemia, pulmonary ischemia, ischemia related to infection, limb ischemia, ischemic cardiomyopathy, cerebrovascular ischemia, and myocardial ischemia. Impacted tissue can be associated with nearly any physiological system including the circulatory system or the central nervous system, e.g., a limb, graft (e.g., muscle or nerve graft), or organ (e.g., heart, brain, kidney and lung). Highly angiogenic endothelial cells may also be utilized in angiogenesis assay kits and in the study of endothelial cells, particularly the functions and permeability of the endothelial cell barrier. In order to determine angiogenic capability and the ability of endothelial cells to form tubes it has been necessary to carry out angiogenesis assays for each lot of endothelial cells. These assays are time consuming and costly. Therefore, there is a need for a cheaper, quicker way to screen for and mark angiogenesis capability among endothelial cells. This need is met by the present invention which provides an effective and cost-efficient means of identifying highly angiogenic endothelial cells.

SUMMARY OF THE INVENTION

The present invention is directed to methods of screening endothelial cell populations for angiogenic capability. One particular embodiment of the invention is directed to a method of screening a primary endothelial cell population for angiogenesis capability comprising measuring the percentage of cells that are positive for VEGF R2 and CD34, the level of VEGF R2, or measuring the VEGF R2/VEGF R1 ratio in the population; and selecting those populations where the measured percentage or measured ratio is over a threshold value. The step of measuring the percentage of cells that are positive for VEGF R2 and CD34 or measuring the VEGF R2/VEGF R1 ratio in the population can, in a preferred embodiment, comprise staining the endothelial cell population with anti-VEGF R2 antibodies and anti-CD34 antibodies or anti-VEGF R2 and anti-VEGF R1 antibodies.

DETAILED DESCRIPTION OF THE INVENTION

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implicated in other compositions and methods, and that any such variation would be within such modifications that do not part from the scope of the present invention. Before explaining the disclosed embodiments of the present invention in detail, it is to be understood that the invention is not limited in its application to the details of any particular embodiment shown, since of course the invention is capable of other embodiments. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

Endothelial cells are the cells that make up the inside of blood vessels. Human and other mammalian endothelial cells are preferred for use in the invention. These include but are not limited to human dermal microvascular endothelial cells and human pulmonary microvascular endothelial cells (HM-VEC) and human umbilical vein endothelial cells (HUVEC).

Angiogenesis capability refers to the capacity of an endothelial cell to generate new capillary blood vessels. An aspect of this capacity is the ability of the endothelial cell to form tubes. This tube-forming is referred to as tubulogenesis.

The present invention is directed, among other things, toward a method of screening endothelial cells for angiogenesis capability using an anti-VEGF antibody. The term "anti-VEGF antibody" refers to an antibody that blocks VEGF activity. Examples of such antibodies the antibodies to human VEGF described by Kim, U.S. Pat. No. 6,582,959, or those described by Thorpe et al., U.S. Pat. No. 6,524,583.

In a preferred embodiment the method of screening endothelial cells comprises measuring the percentage of VEGF R2 positive and CD34 positive cells in each endothelial cell population or measuring the ratio of VEGF R2/VEGF R1 in the population. Populations where the measured percentage or ratio is over a threshold are then selected. These thresholds can be determined with ordinary experimentation correlating the amount or ratio with the desired tubule-forming quality of the cell population.

The VEGF R2 positive cells in each endothelial cell population can be quantified using various known methods, including but not limited to fluorescence activated cell sorting (FACS) analysis, immunofluorescent imaging and data processing or cell-based Enzyme-Linked Immunosorbent Assay (ELISA). Antibodies for use in such methods are well known and readily available, e.g., antibodies directed to vascular endothelial growth factor receptors can be identified and obtained from a variety of sources, such as the MSRS catalog of antibodies (Aerie Corporation, Birmingham, Mich.), and can also be prepared via conventional antibody generation methods.

It is believed that the more VEGF R2 positive and CD34 positive endothelial cells, or the higher VEGF R2 to VEGF R1 ratio, the higher the capability of the endothelial cells to form tubes and the higher the angiogenic capability of the endothelial cells.

In one embodiment of the present invention the method of screening endothelial cells for angiogenic properties comprises staining the human endothelial cells with anti-VEGF R2 receptors and anti-CD34 or with anti-VEGF R1 receptors. In a preferred embodiment after the step of staining the endothelial cells the stained cells are labeled with secondary antibodies. The secondary antibodies are preferably fluorescein or rhodamine conjugated. In one embodiment the stained and labeled endothelial cells are examined using, for example, FACS, fluorescent imaging, or ELISA and the VEGF R2 positive and CD34 positive cells are identified. In a preferred embodiment the percentage of VEGF R2 positive and CD 34 positve cells in each endothelial cell population or the ratio of VEGF R2/VEGF R1 in the population is measured. Endothelial populations are selected such that the percentage of VEGF R2 positive and CD34 positive cells in each endothelial cell population or the ratio of VEGF R2/VEGF R1 in the population is over a certain threshold.

The method of selecting cell populations can also be incorporated into a method of identifying bioactive agents by contacting prospective bioactive agents with the endothelial cells at some time relevant to modulating angiogenic activity. Bioactive agents include substances such as chemicals that can act on a cell, tissue, organ or organism, including but not limited to insecticides or drugs (i.e., pharmaceuticals) to create a change in the functioning of the cell, organ or organism. The time frame can be readily determined experimentally. Bioactive agents that reduce angiogenesis are candidate bioactive agents for disrupting blood cell formation sought to be induced by tumor cells. Bioactive agents that stimulate angiogenesis are candidate bioactive agents to increase vascularization in tissue damaged by ischemic events, tissue whose vascularization has been damaged by environmental factors such as smoking, or pathological factors resulting from, e.g., cardiovascular diseases, diseases of the peripheral arteries as well as vascular and cerebral lesions. The selection method is believed to be particularly applicable to angiogenesis assays that measure tubule formation, though other angiogenesis measures, such as cell migration, can be used. Useful endothelial cell tube formation assays include tube formation on matrices such as Matrigel (Becton-Dickinson, Franklin Lakes, N.J.), fibrin gel or collagen gel and tube formation in co-culture models such endothelial cells co-culture with either tumor cells or normal fibroblast cells. For example, primary human endothelial cells (such as HUVEC and HMVEC cells) can be mixed (e.g., at a ratio of 100:1) with tumor cell U251 (a glioblastoma cell line). The cells can be seeded in 6-well plates at a density of, for example, 1×10e6/well. The co-cultures can be incubated in endothelial cell medium EGM-2 MV (Cambrex, Walkersville, Md.) in a 37° C./5% CO2 incubator and the medium replaced every two days till day 11. Tube formation should be observed on and after day 7.

The method of the invention can further be used to adjust the angiogenic potential of cell populations by mixing populations to achieve the desired amounts or ratio of the markers used in the invention. Or, separation devices such as fluorescence activated cell sorting devices can be used to isolate cell populations enriched in cells expressing VEGF R2 receptor and CD34. The enriched populations can, in turn, be used to adjust the amounts or ratio of the cells expressing the markers used in the invention.

While the invention has been described with an emphasis on particular embodiments thereof, those skilled in the art may make various modifications to the described embodiments of the invention without departing from the scope of the invention. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed:

1. A method of selecting for higher angiogenesis capability among endothelial cells in an endothelial cell population, said method comprising:
   a) staining the endothelial cell population with anti-VEGF R2 and anti-VEGF R1;
   b) measuring the VEGF R2 to VEGF R1 ratio in the stained population; and
   c) selecting endothelial cells having a higher VEGF R2 to VEGF R1 ratio wherein the higher the VEGF R2 to VEGF R1 ratio, the higher the capability of the endothelial cells to form tubes and the higher the angiogenic capability of the endothelial cells.

2. The method of claim 1, wherein the step of measuring the VEGF R2 to VEGF R1 ratio in the stained population comprises fluorescence activated cell sorting analysis.

3. The method of claim 1, wherein the step of measuring the VEGF R2 to VEGF R1 ratio in the stained population comprises immunofluorescent imaging and data processing.

4. The method of claim 1, wherein the step of measuring the VEGF R2 to VEGF R1 ratio in the stained population comprises a cell-based Enzyme-Linked Immunosorbent Assay.

5. The method of claim 1, further comprising labeling the endothelial cell population with one or more secondary antibodies.

6. The method of claim 5, wherein the one or more secondary antibodies are fluorescein or rhodamine conjugated.

7. The method of claim 1, wherein the endothelial cell population comprises human dermal microvascular endothelial cells.

8. The method of claim 1, wherein the endothelial cell population comprises human pulmonary microvascular endothelial cells.

9. The method of claim 1, wherein the endothelial cell population comprises human umbilical vein endothelial cells.

* * * * *